(12) United States Patent
Jennings

(10) Patent No.: US 6,858,735 B2
(45) Date of Patent: Feb. 22, 2005

(54) PREPARATION OF QUINAPRIL HYDROCHLORIDE

(75) Inventor: Sandra Marie Jennings, Gregory, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 10/806,707

(22) Filed: Mar. 23, 2004

(65) Prior Publication Data

US 2004/0192613 A1 Sep. 30, 2004

Related U.S. Application Data

(60) Provisional application No. 60/459,016, filed on Mar. 31, 2003.

(51) Int. Cl.[7] .............................................. C07D 217/12
(52) U.S. Cl. ....................................... 546/147
(58) Field of Search ......................... 546/147

(56) References Cited

U.S. PATENT DOCUMENTS 4,344,949 A * 8/1982 Hoefle et al. ............... 514/307
4,686,295 A * 8/1987 Youssefyeh et al. ......... 548/226
4,761,479 A * 8/1988 Goel et al. .................. 546/147
6,541,635 B1   4/2003 Yu -Lian et al.

FOREIGN PATENT DOCUMENTS

| EP | 0049605 A | 4/1982 |
| EP | 0 065 301 A1 | 11/1982 |
| EP | 0 285 992 A1 | 10/1988 |
| EP | 0 992 495 A1 | 4/2000 |
| GB | 2 095 252 A1 | 9/1982 |
| WO | WO 2002/18321 A | 3/2002 |
| WO | WO 2004/054980 A1 | 7/2004 |

OTHER PUBLICATIONS

Kluthchko et al., "Synthesis of Novel Angiotensin Converting Enzyme Inhibitor Quinapril and RElated Compounds. A Divergence of Structure–Activity Relationships for Non–Sulfhydryl and Sulfhydryl Types," J.Med.Chem. vol. 29, p. 1953 (1986).

* cited by examiner

*Primary Examiner*—Amelia A. Owens
(74) *Attorney, Agent, or Firm*—Matthew J. Russo

(57) ABSTRACT

Methods and materials for preparing quinapril, its pharmaceutically acceptable salts, including quinapril hydrochloride, are disclosed. The method includes reacting (2S,4S)-2-(4-methyl-2,5-dioxo-oxazolidin-3-yl)-4-phenyl-butyric acid ethyl ester with (3S)-1,2,3,4-tetrahydro-isoquinoline-3-carboxylic acid tert-butyl ester to yield quinapril tert-butyl ester, which is subsequently reacted with an acid to yield quinapril or an acid addition salt of quinapril.

6 Claims, No Drawings

PREPARATION OF QUINAPRIL HYDROCHLORIDE

CROSS REFERENCE TO RELATED APPLICATION

This application claims the benefit of U.S. Provisional Patent Application No. 60/459,016, filed Mar. 31, 2003.

BACKGROUND OF THE INVENTION

1. Field of the Invention

This invention relates to materials and methods for preparing (1S,2S,3S)-2-[2-(1-ethoxycarbonyl-3-phenyl-propylamino)-propionyl]-1,2,3,4-tetrahydro-isoquinoline-3-carboxylic acid,

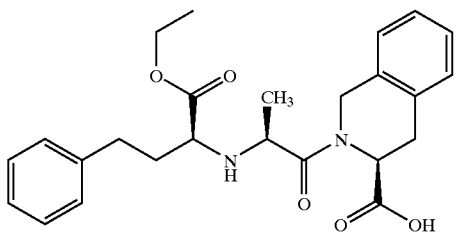

1 which is commonly known as quinapril.

2. Discussion

Quinapril hydrochloride is the active pharmaceutical ingredient in ACCUPRIL® and ACCURETIC®, which are marketed by Pfizer Inc. for treating hypertension and congestive heart failure. Quinapril, and its principal metabolite, quinaprilat (quinapril diacid), are known inhibitors of angiotensin converting enzyme (ACE). ACE is a peptidyl dipeti-dase that catalyzes conversion of angiotensin I to the vasoconstrictor, angiotensin II. See e.g., U.S. Pat. No. 4,344,949 issued to Hoefle et al. (the '949 patent), and U.S. Pat. No. 4,761,479 issued to Goel et al. (the '479 patent). See also Klutchko et al., "Synthesis of Novel Angiotensin Converting Enzyme Inhibitor Quinapril and Related Compounds. A Divergence of Structure-Activity Relationships for Non-Sulfhydryl and Sulfhydryl Types," *J. Med. Chem.* Vol. 29 p. 1553 (1986).

Processes for preparing quinapril and its hydrochloride salt include methods based on the '949 patent and on U.S. Pat. No. 4,686,295 issued to Youssefyeh et al. (the '295 patent). These processes include reacting (3S)-1,2,3,4-tetrahydro-iosoquinoline-3-carboxylic acid benzyl ester (THIQ benzyl ester),

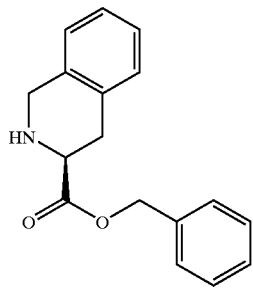

2 with (1S,2S)-2-(1-carboxy-ethylamino)-4-phenyl-butyric acid ethyl ester,

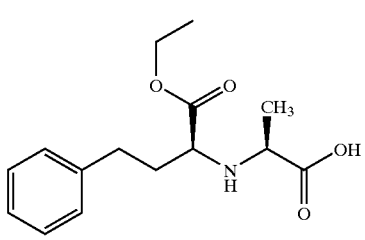

3 or with (2S,4S)-2-(4-methyl-2,5-dioxo-oxazolidin-3-yl)4-phenyl-butyric acid ethyl ester,

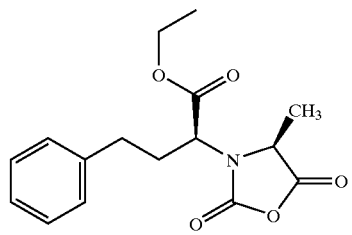

4 to yield (1S,2S,3S)-2-[2-(1-ethoxycarbonyl-3-phenyl-propylamino)-propionyl]-1,2,3,4-tetrahydro-isoquinoline-3-carboxylic acid benzyl ester,

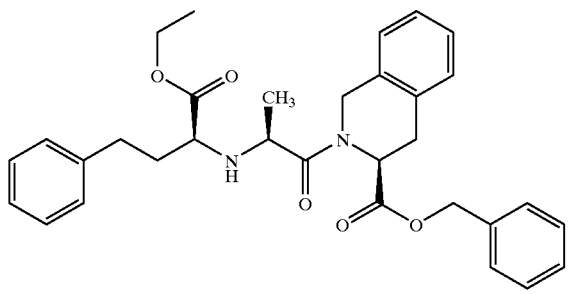

5

Both reactions are carried out in an aprotic solvent, such as methylene chloride. The reaction involving the N-substituted amino acid (Formula 3) includes the use of a coupling agent (e.g., dicyclohexylcarbodiimide) and a catalyst (e.g., N-hydroxybenzotriazole), whereas the reaction involving the N-carboxyanhydride (Formula 4) employs catalytic amounts of an acid.

Following treatment with a mixture of HCl and a solvent, the benzyl protecting group of Formula 5 is subsequently removed via Pd/C-catalyzed hydrogenolysis to yield upon workup, the hydrochloride salt of quinapril,

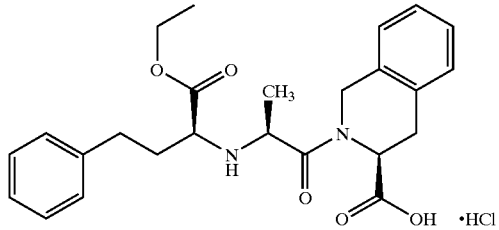

6

The synthetic routes based on the '949 and '295 patents employ readily available starting materials (Formula 2–Formula 4), but suffer a 20% to 40% yield loss based on the limiting reactant. The yield loss has been attributed to intramolecular cyclization (aminolysis) of quinapril (Formula 1) or its benzyl ester (Formula 5) to a diketopiperazine. See G. Guo et al., "Physical Characteristics and Chemical Degradation of Amorphous Quinapril Hydrochloride," *J. Pharm. Sci.* Vol. 89 p. 128 (2000). Diketopiperazine formation is accelerated at temperatures above about 45° C. and is thought to occur primarily during distillation to remove the hydrogenolysis solvent.

The present invention is directed to overcoming, or reducing the effects of, one or more of the problems described above.

SUMMARY OF THE INVENTION

The present invention provides materials and methods for preparing quinapril (Formula 1), quinapril HCl (Formula 6), and other pharmaceutically acceptable salts, including amorphous and crystalline salt forms. Compared to existing methods, the claimed process produces quinapril and its salts in substantially higher yield (approximately 25% greater yield), which results in significant cost savings. Additionally, the method eliminates the need for hydrogenolysis, thereby obviating difficulties associated with handling hydrogen and significantly increasing process throughput. Indeed, the present invention provides an approximately three-fold increase in throughput when using existing equipment.

Thus, one aspect of the present invention provides a method of making a compound of Formula 1,

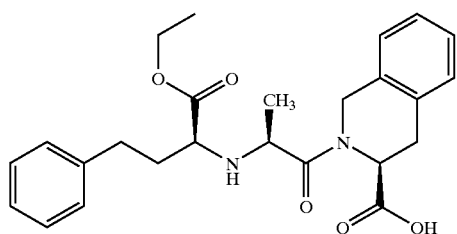

1 or a pharmaceutically acceptable salt of the compound of Formula 1. The method includes reacting a compound of Formula 4,

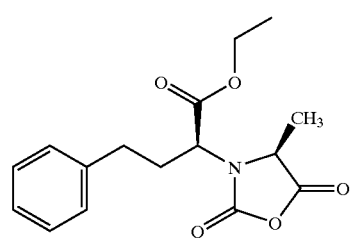

4 with a compound of Formula 7,

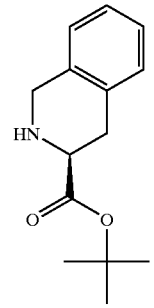

7 to yield a compound of Formula 8,

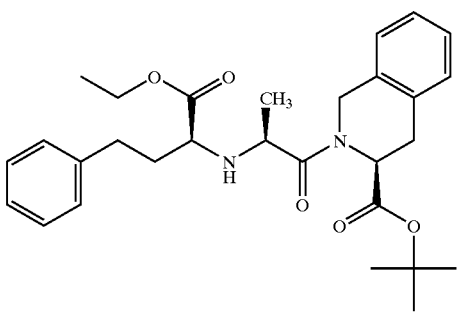

8 which is subsequently contacted with an acid to yield the compound of Formula 1 or a pharmaceutically acceptable salt thereof.

Another aspect of the present invention provides a method of making a compound of Formula 6,

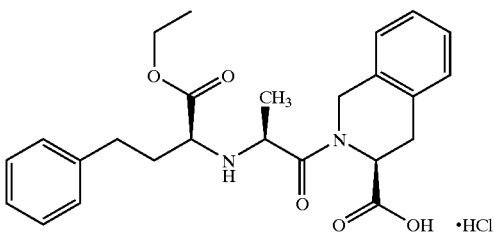

6 and includes reacting the compound of Formula 4 with the compound of Formula 7 to yield the compound of Formula 8 (as described above). The method also includes contacting the compound of Formula 8 with HCl to yield the compound of Formula 6.

A further aspect of the present invention includes a method of making an amorphous form of the compound of Formula 6. The method includes reacting the compound of Formula 4 with the compound of Formula 7 to yield the compound of Formula 8 (as described above). The method also includes contacting the compound of Formula 8 with HCl and with acetone to yield a compound of Formula 9,

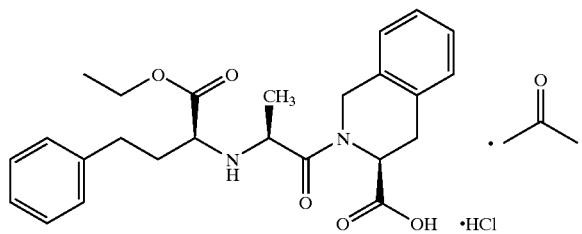

and subsequently recrystallizing the compound of Formula 9 from a polar aprotic solvent to yield an amorphous form of the compound of Formula 6 upon drying.

DETAILED DESCRIPTION

The following table lists abbreviations used through the specification:

| Abbreviation | Description |
| --- | --- |
| DCC | Dicyclohexylcarbodiimide |
| DMSO | Dimethylsulfoxide |
| EtOH | ethanol |
| h, min, s | hours, minutes, and seconds |
| HOAc | acetic acid |
| HOBt | N-hydroxybenzotriazole |
| MeCl$_2$ | methylene chloride |
| MeOH | methanol |
| PTSA | p-toluenesulfonic acid |
| RT | room temperature, from about 20° C. to about 25° C., inclusive |
| THIQ | (3S)-1,2,3,4-tetrahydro-isoquinoline-3-carboxylic acid |
| THF | tetrahydrofuran |

Scheme I illustrates a method for preparing an amorphous hydrochloride salt of quinapril (Formula 6). The method, which can be easily modified to make the free base (Formula 1) or other salts and polymorphs, includes reacting (2S,4S)-2-(4-methyl-2,5-dioxo-oxazolidin-3-yl)-4-phenyl-butyric acid ethyl ester (Formula 4) with (3S)-1,2,3,4-tetrahydro-isoquinoline-3-carboxylic acid tert-butyl ester (Formula 7) in the presence of catalytic amounts of an acid (e.g., HOAc, trifluoroacetic acid, or an acid having similar pKa) to yield quinapril tert-butyl ester, (1S,2S,3S)-2-[2-(1-ethoxycarbonyl-3-phenyl-propylamino)-propionyl]-1,2,3,4-tetrahydro-isoquinoline-3-carboxylic acid tert-butyl ester (Formula 8).

The reaction is carried out in one or more aprotic or protic solvents at a temperature less than about 60° C., and more typically, at a temperature less than or equal to about 45° C. Although lower reaction temperatures help minimize formation of undesirable side-products, the reaction is usually carried out at a temperature of about 15° C. or greater to ensure substantially complete conversion in a reasonable amount of time (i.e., less than 3 h). Thus, the reaction temperature typically ranges from about 15° C. to about 45° C., inclusive, and more typically ranges from about 30° C. to about 35° C., inclusive. Useful aprotic solvents include, without limitation, aromatic solvents such as toluene; haloalkyls such as MeCl$_2$, chloroform, and the like; cyclic or acyclic ethers, such as THF, diethyl ether, and dimethoxyethane; and ketones such as acetone, 2-butanone, and the like. Useful protic solvents include, without limitation, alcohols such as MeOH, EtOH, and the like; alkyl esters such as ethyl acetate; and water.

THIQ tert-butyl ester (Formula 7) can be obtained from CHEMICREA as a p-toluenesulfonic acid salt (THIQ tert-butyl ester PTSA salt), and is prepared by extraction with water and an organic solvent (e.g., toluene) under basic conditions (e.g., pH 8 to pH 9), followed by distillation of the organic phase. Unless stated otherwise, any reference in the disclosure to a temperature range, a pH range, etc., includes the indicated endpoints.

Following the coupling of the N-carboxyanhydride (Formula 4) and THIQ tert-butyl ester (Formula 7), the tert-butyl protecting group is removed by reacting quinapril tert-butyl ester (Formula 8) with aqueous or anhydrous hydrochloric acid. The reaction is carried out in one or more aprotic or protic solvents (e.g., HOAc, MeCl$_2$, toluene, etc.) at approximately RT and yields solution-phase quinapril hydrochloride. The amount of organic solvent added to the reaction mixture is large enough to prevent precipitation of reaction mixture components, but is small enough to obviate the need for subsequent removal by distillation, thereby minimizing the formation of diketopiperazine. Although the tert-butyl group may be removed using other acids, reacting THIQ tert-butyl ester with HCl allows for deprotection and hydrochloride salt formation in a single step.

After forming solution-phase quinapril hydrochloride salt, the reaction mixture is placed under vacuum at about RT to vent residual hydrogen chloride. Acetone is added to the solution, which is cooled to a temperature of about 0° C. to precipitate quinapril HCl as an acetone solvate (Formula 9). The resulting crystalline solid is separated from the mixture by filtration (e.g., centrifugal filtration) and is subsequently recrystallized in a polar aprotic solvent, such as acetonitrile. The recrystallized solvate is subsequently dried to give an amorphous solid. The method gives amorphous quinapril HCl in good yield (i.e., 90% yield based on THIQ tert-butyl ester PTSA salt).

In addition to quinapril (Formula 1), other disclosed compounds are capable of forming pharmaceutically acceptable salts (including disalts). These salts include, without limitation, acid addition salts and base salts. Pharmaceutically acceptable acid addition salts may include nontoxic salts derived from inorganic acids such as hydrochloric, nitric, phosphoric, sulfuric, hydrobromic, hydroiodic, hydrofluoric, phosphorous, and the like, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like.

Pharmaceutically acceptable base salts may include nontoxic salts derived from bases, including metal cations, such as an alkali or alkaline earth metal cation, as well as amines. Examples of suitable metal cations include, without limitation, sodium cations (Na$^+$), potassium cations (K$^+$), magnesium cations (Mg$^{2+}$), calcium cations (Ca$^{2+}$), and the like. Examples of suitable amines include, without limitation, N,N'dibenzylethylenediamine, chloroprocaine, choline, diethanolamine, dicyclohexylamine, ethylenediamine, N-methylglucamine, and procaine. For a discussion of useful acid addition and base salts, see S. M. Berge et al., "Pharmaceutical Salts," *J. of Pharm. Sci.*, Vol. 66 p. 1–19 (1977); see also Stahl and Wermouth, *Handbook of Pharmaceutical Salts: Properties, Selection, and Use* (2002).

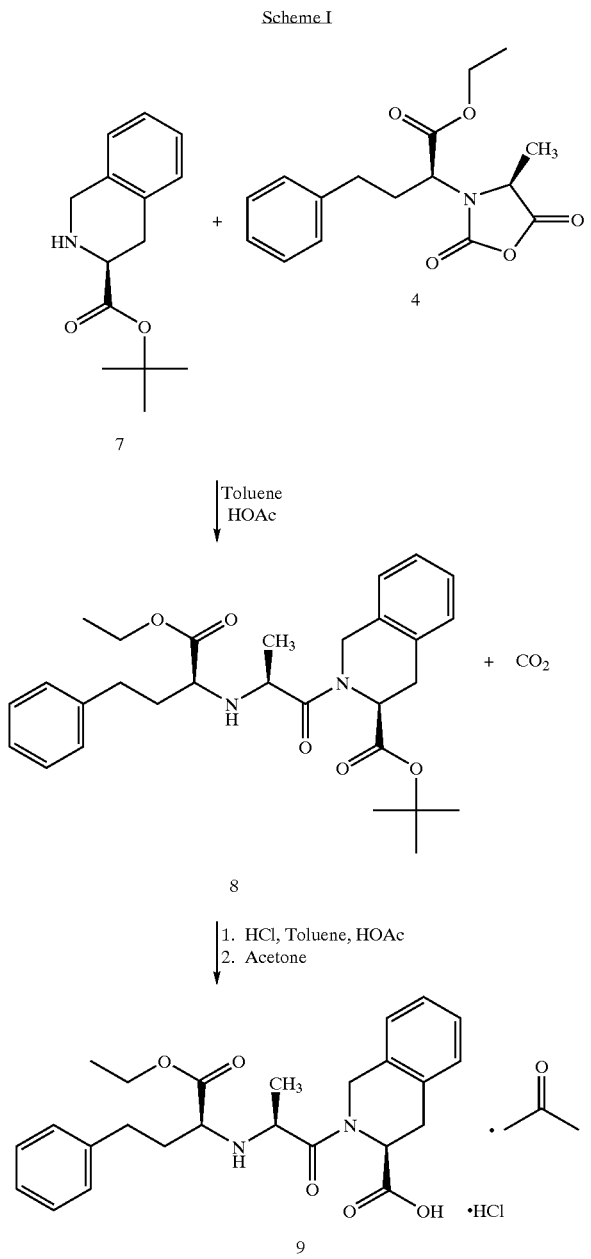

Scheme I

Generally, one may prepare a pharmaceutically acceptable acid addition salt (or base salt) by contacting a compound's free base (or free acid) with a sufficient amount of a desired acid (or base) to produce a nontoxic salt. One may then isolate the salt by filtration if it precipitates from solution, or by evaporation to recover the salt. One may also regenerate the free base (or free acid) by contacting the acid addition salt with a base (or the base salt with an acid). Though certain physical properties of the free base (or free acid) and its respective acid addition salt (or base salt) may differ (e.g., solubility, crystal structure, hygroscopicity, etc.), a compound's free base and acid addition salt (or its free acid and base salt) are otherwise equivalent for purposes of this disclosure.

As indicated above and in the examples below, quinapril hydrochloride is isolated as an acetone solvate (Formula 9). Certain other compounds of this disclosure may exist as an unsolvated form or as a solvated form, including hydrated forms. Pharmaceutically acceptable solvates include hydrates and solvates in which the crystallization solvent may be isotopically substituted, e.g. $D_2O$, $d_6$-acetone, $d_6$-DMSO, etc. Generally, the solvated forms, including hydrated forms, are equivalent to unsolvated forms for the purposes of this disclosure. Thus, unless expressly noted, all references to the free base, the free acid or the unsolvated form of a compound also includes the corresponding acid addition salt, base salt or solvated form of the compound.

The disclosed compounds also include all pharmaceutically acceptable isotopic variations, in which at least one atom is replaced by an atom having the same atomic number, but an atomic mass different from the atomic mass usually found in nature. Examples of isotopes suitable for inclusion in the disclosed compounds include, without limitation, isotopes of hydrogen, such as $^2H$ and $^3H$; isotopes of carbon, such as $^{13}C$ and $^{14}C$; isotopes of nitrogen, such as $^{15}N$; isotopes of oxygen, such as $^{17}O$ and $^{18}O$; isotopes of phosphorus, such as $^{31}P$ and $^{32}P$; isotopes of sulfur, such as $^{35}S$; isotopes of fluorine, such as $^{18}F$; and isotopes of chlorine, such as $^{36}Cl$. Use of isotopic variations (e.g., deuterium, $^2H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3H$, or $^{14}C$), which may be useful in drug and/or substrate tissue distribution studies.

EXAMPLES

The following examples are intended to be illustrative and non-limiting, and represent specific embodiments of the present invention.

Example 1

THIQ tert-butyl ester

Sodium hydroxide (5.9 kg, 50% aq soln by wt), toluene (56 L) and water (28 L) were added to a glass-lined still containing THIQ tert-butyl ester PTSA salt (30 kg) and water (28 L). The resulting mixture was agitated at RT for about 10 min to dissolve the solids. The mixture was allowed to separate into aqueous and organic layers. Aliquots of HCl (37% aq soln by wt) or NaOH (50% aq soln by wt) were added to maintain a pH between about 8 and 9, inclusive, in the aqueous layer. Following the last addition of HCl or NaOH, the mixture was agitated for an additional 30 min, and the aqueous and organic layers were allowed to settle for 15 min. The lower aqueous layer was drawn off, and the remaining organic layer was distilled under a vacuum of about 5 mm Hg until the volume of the organic mixture reached about 14 L. The resulting THIQ tert-butyl ester solution was cooled to below RT and was placed in a glass-lined transfer vessel. The interior of the still was rinsed with toluene (2 L) to recover residual THIQ tert-butyl ester, which was returned to the transfer vessel.

Example 2

Quinapril tert-butyl ester

The THIQ tert-butyl ester of Example 1 was added over about a five-minute period, with agitation, to a glass-lined still containing (2S,4S)-2-(4-methyl-2,5-dioxo-oxazolidin-3-yl)4-phenyl-butyric acid ethyl ester (23.5 kg), toluene (12 L), and HOAc (0.09 kg). The interior of the transfer vessel was rinsed with toluene (7 L) to recover residual THIQ tert-butyl ester, which was returned to the still. The still contents were agitated for at least 30 min at temperature between about 30° C. and 35° C. to permit substantially complete conversion (≧99.9%) of THIQ tert-butyl ester to quinapril tert-butyl ester. The reaction mixture was subsequently cooled to a temperature between about 15° C. and 25° C. During conversion of THIQ tert-butyl ester to quinapril tert-butyl ester, $CO_2$ was generated, which was vented to the atmosphere.

Example 3

Quinapril HCl Solution

Acetic acid (10.5 kg) was added to the quinapril tert-butyl ester reaction mixture of Example 2, which had been cooled to a temperature between about -5° C. and 5° C. Following the addition of HOAc, anhydrous hydrogen chloride (8.1 kg) was added to the reaction mixture, with agitation, at a rate that maintained the pressure in the still headspace of less than about 5 psig. During the addition of HCl, the reaction mixture was cooled to maintain a temperature less than or equal to about 20° C. Isobutylene, which was formed during the deprotection reaction, was vented to a caustic scrubber whenever the pressure in the still headspace reached about 10 psig. Following the addition of HCl, the reaction mixture was agitated at a temperature between about 20° C. and 25° C. until substantially all (≧99.5%) of the quinapril tert-butyl ester had been converted to quinapril HCl.

Example 4

Acetone Solvate of Quinapril HCl

Following the addition of acetone (75 L) to the quinapril HCl solution of Example 3, the headspace of the still was evacuated to remove excess HCl. The reaction mixture was subsequently cooled to a temperature between about 10° C. and 20° C. to promote crystallization of the acetone solvate of quinapril HCl. Following the onset of crystallization, the contents of the still were agitated at a temperature between about 15° C. and 25° C. for at least 8 h, and subsequently at a temperature between about -5° C. and 5° C. for at least 2 h. The contents of the still were transferred to a centrifuge to isolate the crystalline acetone solvate of quinapril HCl. To recover residual quinapril HCl, the still was charged with acetone (20 L) and was cooled to a temperature between about 0° C. and 10° C. The resulting acetone rinse was transferred to the centrifuge to wash the crystals. $^{13}$C nuclear magnetic resonance spectrum (DMSO-$d_6$): δ13.65, 14.48, 29.82, 30.43, 30.51 (acetone), 31.06, 43.36, 44.35, 51.77, 52.44, 52.96, 53.73, 57.14, 61.83, 126.08, 126.54, 127.95, 128.23, 128.29, 131.91, 132.24, 132.36, 140.09, 168.20, 171.11, 171.24, 208.16 (acetone) ppm.

Example 5

Quinapril HCl (Amorphous)

Acetonitrile, which had been pre-heated to a temperature between about 75° C. and 82° C., was added to a glass-lined vessel containing quinapril HCl acetone solvate of Example 4. The amount of acetonitrile added was about 3.5 times the mass of the quinapril HCl acetone solvate, which was an amount sufficient to completely dissolve the solid. The contents of the vessel were agitated and heated to a temperature between about 75° C. and 82° C. for less than 10 min, and the resulting solution was transferred to a glass-lined still through a filter. The contents of the still were agitated at a temperature between about 0° C. and 5° C. for at least 8 h in order to crystallize the quinapril HCl acetonitrile solvate. The contents of the still were transferred to a centrifuge, where the quinapril HCl acetonitrile solvate was collected in a 1–3 micron polyethylene centrifuge bag. To recover residual quinapril HCl acetonitrile solvate, the still was charged with acetonitrile (10 kg) and was cooled to a temperature of about 5° C. or less. The resulting acetonitrile rinse was transferred to the centrifuge to wash the solids, which were subsequently dried under a vacuum of about 5 mm Hg and at a temperature between about 50° C. and 55° C. until the acetonitrile and acetone levels in the solids were less than 0.041 wt % and 0.25 wt %, respectively. During the drying process, the crystalline quinapril HCl acetonitrile solvate was converted to amorphous quinapril HCl. The overall yield, based on the amount of THIQ tert-butyl ester PTSA salt was about 90%. 13C nuclear magnetic resonance spectrum (DMSO-$d_6$): δ13.79, 14.59, 29.92, 30.37, 30.53 43.47, 44.41, 51.84, 52.52, 53.02, 53.81, 57.18, 61.93, 126.21, 126.67, 127.08, 128.20, 128.37, 131.50, 132.06, 132.47, 140.23, 168.41, 171.31, 171.43 ppm.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patents, patent applications, and publications, are herein incorporated by reference in their entirety and for all purposes.

What is claimed is:

1. A method of making a compound of Formula 1,

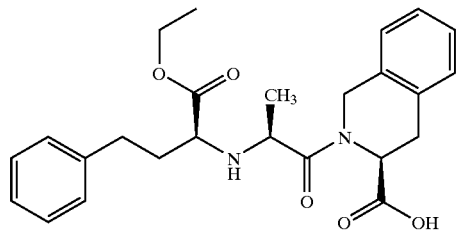

or a pharmaceutically acceptable salt thereof, the method comprising:

reacting a compound of Formula 4,

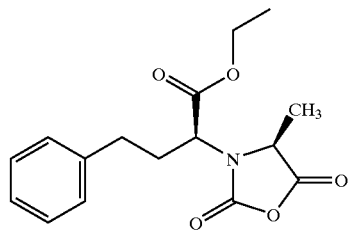

with a compound of Formula 7,

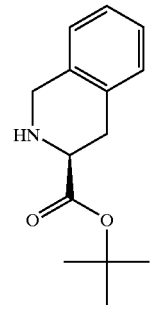

to yield a compound of Formula 8,

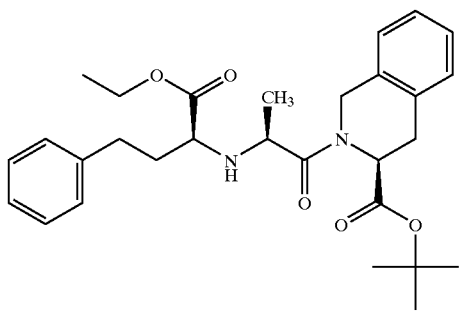

and contacting the compound of Formula 8 with an acid to yield the compound of Formula 1 or a pharmaceutically acceptable salt thereof.

2. The method of claim 1, further comprising contacting the pharmaceutically acceptable salt of the compound of Formula 1 with a solvent to yield a solvate.

3. The method of claim 2, further comprising drying the solvate.

4. A method of making a compound of Formula 6,

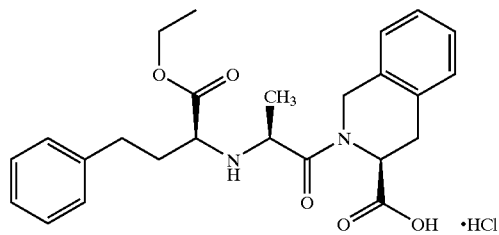

the method comprising:

reacting a compound of Formula 4,

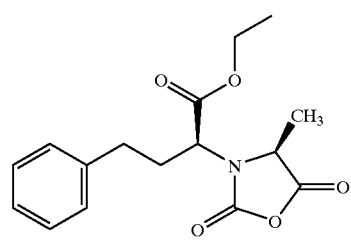

with a compound of Formula 7,

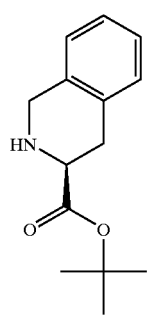

to yield a compound of Formula 8,

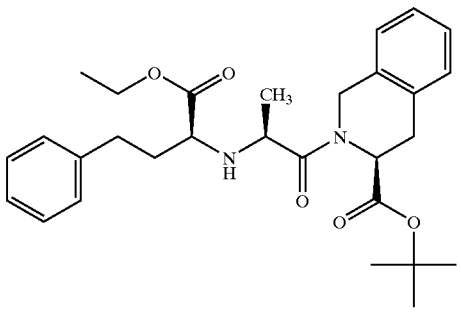

and contacting the compound of Formula 8 with HCl to yield the compound of Formula 6.

5. A method of making a compound of Formula 6,

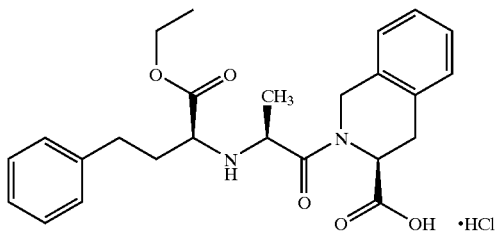

the method comprising:

reacting a compound of Formula 4,

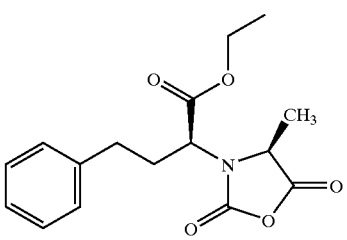

with a compound of Formula 7,

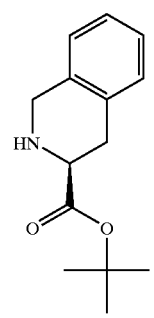

to yield a compound of Formula 8,

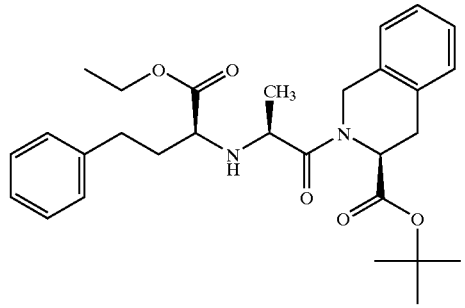

8 contacting a compound of Formula 8 with HCl and with acetone to yield the compound of Formula 9,

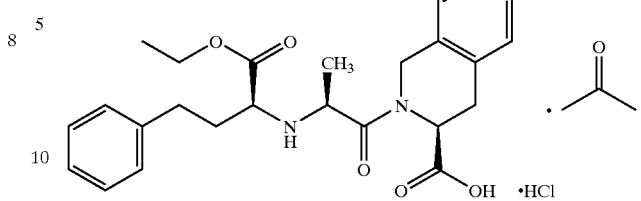

9 recrystallizing the compound of Formula 9 from a polar aprotic solvent to yield a solvate, and drying the solvate to yield an amorphous form of the compound of Formula 6.

6. The method of claim 5, further comprising recrystallizing the compound of Formula 9 from acetonitrile.

* * * * *